United States Patent
Mintchev

(10) Patent No.: US 12,194,204 B2
(45) Date of Patent: Jan. 14, 2025

(54) SYSTEM AND METHOD FOR DYNAMICALLY REDUCING MICROBIOLOGICAL CONTAMINANTS IN THE VICINITY OF PERSONAL EQUIPMENT

(71) Applicant: Martin Mintchev, Calgary (CA)

(72) Inventor: Martin Mintchev, Calgary (CA)

(*) Notice: Subject to any disclaimer, the term of this patent is extended or adjusted under 35 U.S.C. 154(b) by 816 days.

(21) Appl. No.: 17/214,837

(22) Filed: Mar. 27, 2021

(65) Prior Publication Data

US 2021/0213154 A1 Jul. 15, 2021

Related U.S. Application Data

(60) Provisional application No. 62/704,171, filed on Apr. 25, 2020.

(51) Int. Cl.
*A61L 9/20* (2006.01)
*A62B 18/00* (2006.01)

(52) U.S. Cl.
CPC .............. *A61L 9/20* (2013.01); *A62B 18/003* (2013.01); *A61L 2209/111* (2013.01); *A61L 2209/15* (2013.01)

(58) Field of Classification Search
CPC ......... A62B 18/00; A62B 18/003; A61L 9/00; A61L 9/16; A61L 9/18; A61L 9/20; A61L 9/22; A61L 2202/11; A61L 2202/122; A61L 2202/14; B01D 2257/91; B01D 2259/804; C02F 2201/3222; A61M 2202/203; A61M 2202/206; A61N 2205/053; A61G 10/02; A42B 1/24; A42B 1/242; A42B 1/244; A42B 3/0433; A42B 3/044; A42B 3/0446; Y02A 50/00; Y02A 50/20; Y02A 50/30; A41D 2400/28
See application file for complete search history.

(56) References Cited

U.S. PATENT DOCUMENTS

| | | | |
|---|---|---|---|
| 8,733,356 B1* | 5/2014 | Roth | A62B 18/003 128/205.27 |
| 9,700,072 B2* | 7/2017 | Dobrinsky | A23L 3/28 |
| 2019/0099613 A1* | 4/2019 | Estes | A61N 5/0616 |
| 2021/0285633 A1* | 9/2021 | Esmailzadeh | A42B 1/242 |
| 2021/0298380 A1* | 9/2021 | Brown, II | A42B 1/0181 |
| 2021/0299297 A1* | 9/2021 | Roeder, Jr. | F21V 21/084 |
| 2021/0322620 A1* | 10/2021 | Tillmanns | A61L 9/20 |
| 2023/0173117 A1* | 6/2023 | Tung | A41D 13/1184 128/858 |
| 2024/0042075 A1* | 2/2024 | Imamura | A61L 2/10 |

FOREIGN PATENT DOCUMENTS

WO WO-2021211723 A1 * 10/2021 ............... A23L 3/28

OTHER PUBLICATIONS

Machine Translation of WO-2021211723-A1. Accessed from PE2E Search tool on Dec. 2023. (Year: 2021).*

* cited by examiner

Primary Examiner — Kendra D Carter
Assistant Examiner — Jaeick Jang
(74) Attorney, Agent, or Firm — Ryan W Dupuis; Ade & Company Inc.

(57) ABSTRACT

Personal equipment having a radiation source or an array of radiation sources for creating an aura of radiation in the vicinity of the user. The created aura is oriented in space, such as to be safe for the user but harmful to microbiological contaminants present in the air in the vicinity of the user and bombarding the user in routine situations.

2 Claims, 5 Drawing Sheets

SYSTEM AND METHOD FOR DYNAMICALLY REDUCING MICROBIOLOGICAL CONTAMINANTS IN THE VICINITY OF PERSONAL EQUIPMENT

CROSS-REFERENCE TO RELATED APPLICATIONS

This application claims priority to the U.S. provisional patent application Ser. No. 62/704,171, filed on Apr. 25, 2020, which is incorporated herein by reference in its entirety.

FIELD OF THE INVENTION

The present invention relates to personal equipment having a microbiocidal radiation source. More particularly, the present invention relates to personal equipment having an embedded microbiocidal radiation source configure to create an aura of microbiocidal interfering radiations in the vicinity of the personal equipment.

BACKGROUND OF THE INVENTION

Air-borne microorganisms, such as bacteria, viruses, and other potentially harmful pathogens cause various infections, epidemics, and pandemics, some of which are deadly and responsible for the deaths of millions of people each year. Many epidemics are known to vanish entire civilizations from the Earth. Besides several advancements and discoveries in the medical field, pathogenic microorganisms are still a major threat to humans. Recent Covid-19 coronavirus pandemic resulted in millions of deaths and severely impacted the social and economic health of the countries.

According to the Centers for Disease Control (CDC), air-borne contagious diseases cause over 70 million illnesses, over 1,000,000 hospitalizations, and over 50,000 deaths in the United States each year. A variety of different disease-causing microorganisms, such as influenza and coronaviruses, *Escherichia coli*, and *Staphylococcus aureus*, can be transmitted by dirty hands or by airborne particles directly entering the body through the mouth, nose, ears, and eyes upon close contact with contaminated objects or pathogen-carrying subjects. Hospital-acquired infections are also a major concern for the medical professionals since such infections are hard and resistant to known antibiotics. Similarly, laboratories wherein the infections and pathogens are investigated are also at a greater risk of spreading infections.

Disinfecting wipes, regular hand washing, quarantines, and social distancing are effective in reducing some types of microorganisms. However, these measures are too cumbersome for regular use, and their continuous utilization poses huge problems in terms of the normal daily functioning of the society, particularly in professional, industrial, sports, and hospital settings. In many situations, users wear special headgear, garments, goggles, masks, shoes, and gloves to reduce the spread of germs, particularly in critical hospital and industrial settings. However, as the recent COVID-19 pandemic demonstrated, about 10 to 20% of the hospital personnel got exposed to the coronavirus despite wearing full protective gear and following all prescribed disinfection routines, very often at the price of significant and tedious scrubbing and decontamination procedures, nevertheless resulting in breakdowns, failures, and therefore, more infections.

Thus, a long-term need is there for an effective mechanism to prevent the spread of infections between people without affecting the daily routine or activities of users.

SUMMARY OF THE INVENTION

The following presents a simplified summary of one or more embodiments of the present invention in order to provide a basic understanding of such embodiments. This summary is not an extensive overview of all contemplated embodiments and is intended to neither identify key or critical elements of all embodiments nor delineate the scope of any or all embodiments. Its sole purpose is to present some concepts of one or more embodiments in a simplified form as a prelude to the more detailed description that is presented later.

The principal object of the present invention is directed to the personal equipment of a user having embedded radiation sources or an array of radiation sources, the specific radiation sources emitting ultraviolet light radiation in the C wavelength domain (UV-C radiation).

It is another object of the present invention that the personal equipment dynamically protects a user from airborne microorganisms.

It is still another object of the present invention that the personal equipment protects the user without affecting the daily routine of the user.

It is yet another object of the present invention that the personal equipment protects the user without affecting the activity or attention of the user.

It is a further object of the present invention that the personal equipment can be related to utility articles of the user, such as clothing.

It is still a further object of the present invention that the disclosed personal equipment can reduce the spread of airborne pathogenic infections between persons.

It is an additional object of the present invention that the personal equipment is economic to manufacture.

In one aspect, disclosed is personal equipment with integrated UV-C radiation sources or an array of the UV-C radiation sources for a user. The UV-C radiation sources create an aura of UV-C radiation in the vicinity of the user reducing the microbial load in the air.

In one aspect, the aura of the UV-C radiations is oriented so that the user is not exposed to the radiation. Moreover, the intensity of the UV-C radiation is such as to be harmful to the microorganisms and pathogens, including viruses, but safe for humans.

In one aspect, the personal equipment can be any utility article of use for a user, such as clothing and wearable accessories. The personal equipment can also include a power source for powering the UV-C radiation source and a controller. The controller can be used to turn the UV-C radiation/light sources on and off. Moreover, the controller can also allow adjusting the number of UV-C sources that activate at one time or the intensity of the UV-C sources, including their interference. Modification of the UV-C light sources may allow adjusting the zone of the UV-C radiation aura around the user.

In one aspect, the personal equipment can also include sensors to detect the presence of another person in proximity and to determine the distance between the user and another person. The controller can turn off the UV-C sources or decrease the intensity, so that the approaching person may not be exposed to the UV-C radiation or turn on the UV-C sources or increase intensity so that the approaching person can maintain pre-programmed social distancing.

In one aspect, the UV source can be embedded in the personal equipment but positioned such as to emit the UV radiations away from the exposed skin of the user.

In one aspect, the personal equipment can monitor whether the user is about to be in contact with external subjects and/or objects at a distance lesser than a pre-programmed level. The controller can turn on the UV aura when the external subjects and/or objects are within the pre-determined range and can turn the UV aura off when the external subjects and/or objects leave the vicinity of the user.

A more complete understanding of the present invention, as well as further features and advantages of the present invention, will be obtained by reference to the following detailed description and drawings.

These and other objects and advantages of the embodiments herein and the summary will become readily apparent from the following detailed description taken in conjunction with the accompanying drawings.

BRIEF DESCRIPTION OF THE DRAWINGS

The accompanying figures, which are incorporated herein, form part of the specification and illustrate embodiments of the present invention. Together with the description, the figures further explain the principles of the present invention and enable a person skilled in the relevant arts to make and use the invention.

DETAILED DESCRIPTION

Figure 1:
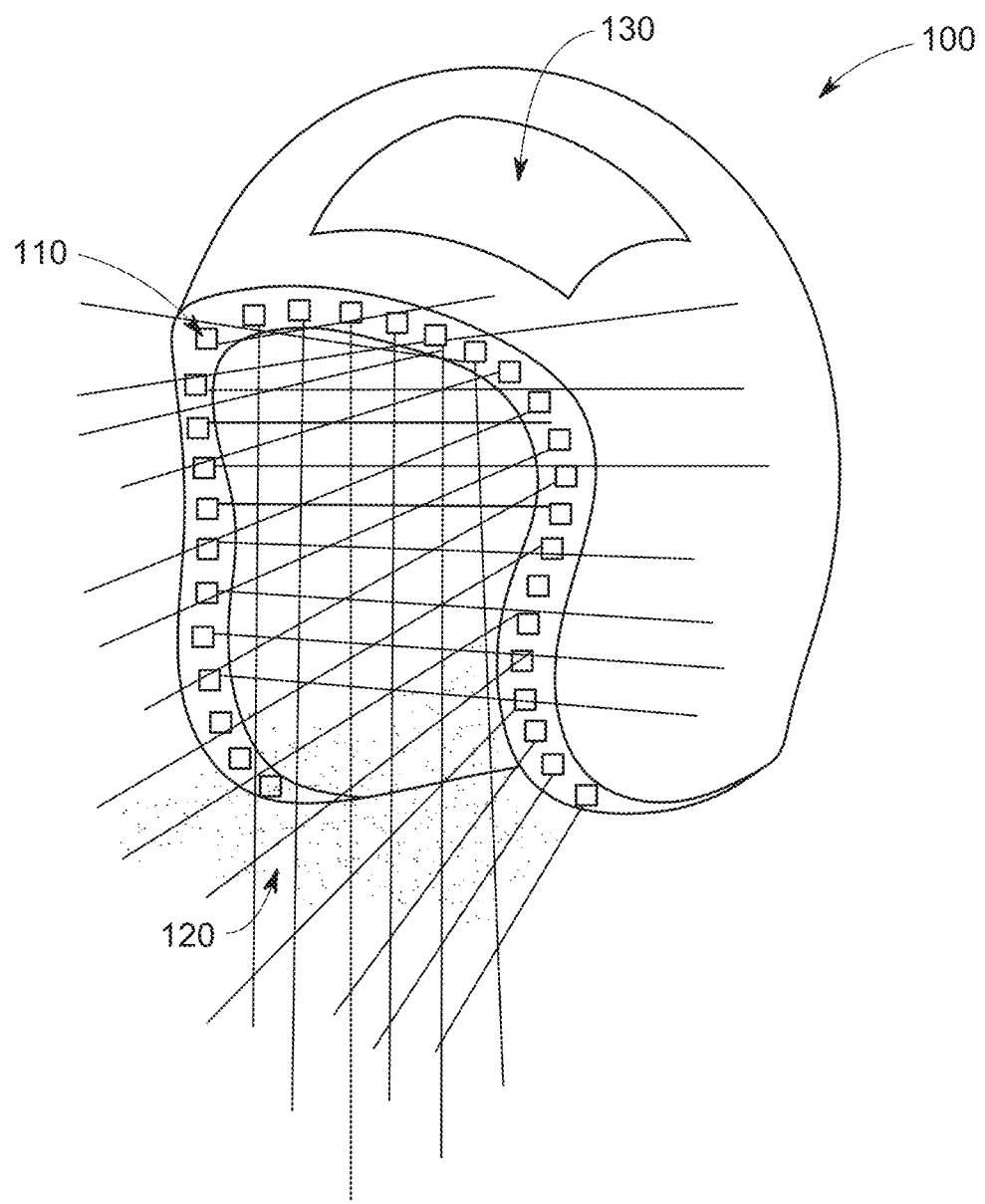
FIG. 1 shows an exemplary embodiment of the personal equipment which is a helmet with an array of UV light emitting diodes (LEDs) for creating a UV aura in the proximity of the wearer's face, according to the present invention.

Subject matter will now be described more fully hereinafter with reference to the accompanying drawings, which form a part hereof, and which show, by way of illustration, specific exemplary embodiments. Subject matter may, however, be embodied in a variety of different forms and, therefore, covered or claimed subject matter is intended to be construed as not being limited to any exemplary embodiments set forth herein; exemplary embodiments are provided merely to be illustrative. Likewise, a reasonably broad scope for claimed or covered subject matter is intended. Among other things, for example, the subject matter may be embodied as methods, devices, components, or systems. The following detailed description is, therefore, not intended to be taken in a limiting sense.

The word "exemplary" is used herein to mean "serving as an example, instance, or illustration." Any embodiment described herein as "exemplary" is not necessarily to be construed as preferred or advantageous over other embodiments. Likewise, the term "embodiments of the present invention" does not require that all embodiments of the invention include the discussed feature, advantage, or mode of operation.

The terminology used herein is for the purpose of describing particular embodiments only and is not intended to be limiting of embodiments of the invention. As used herein, the singular forms "a", "an" and "the" are intended to include the plural forms as well, unless the context clearly indicates otherwise. It will be further understood that the terms "comprises", "comprising,", "includes" and/or "including", when used herein, specify the presence of stated features, integers, steps, operations, elements, and/or components, but do not preclude the presence or addition of one or more other features, integers, steps, operations, elements, components, and/or groups thereof.

The following detailed description includes the best currently contemplated mode or modes of carrying out exemplary embodiments of the invention. The description is not to be taken in a limiting sense but is made merely for the purpose of illustrating the general principles of the invention, since the scope of the invention will be best defined by the allowed claims of any resulting patent.

Disclosed is personal equipment having a UV light source or an array of UV light sources that can create an aura of UV radiation in a spatial relationship with the personal equipment for decreasing the air dispersed microbiological load (including viral load) near the personal equipment. Personal equipment can be any utility article for a user, such as clothing, furniture, clothing accessory, footwear, personal electronic equipment, and the like. The utility article can be related to a user for use in his/her daily routine. Examples of personal equipment can include clothing articles, such as gown, shirt, dress, pants, vest, jacket; clothing accessories, such as cap, belt, bracelet, watch; utility articles, such as helmet, bed, pillow, sheet, blanket; and furniture, such as car seat, office chair, table, sofa, seating arranged in public places, restaurants, and the like.

The UV radiation source can be UV LEDs that can be embedded in the personal equipment, such as along its periphery. The UV LEDs can be spaced in an array in the personal equipment, such as along the periphery of the personal equipment. The UV array can be of a type and arrangement such as to produce an aura of interfering UV radiations in spatial relationship with the physical equipment. The energy of the aura can be sufficient for having the microbiocidal action. The aura produced in the immediate vicinity of the personal equipment can in near-real-time reduce the harmful microbiological load contained in the air coming in contact with personal equipment and the user associated with the personal equipment. The range of the aura zone and the intensity of the UV radiations, including their pattern of interference, can be varied automatically or manually, both methods are within the scope of the present invention. For example, the air the user inhales or exhales can be irradiated by the UV aura to reduce the microbial load. Moreover, the objects about to come in contact with the user associated with the personal equipment can be irradiated with the aura before the user touches the object. In one case, the aura can also dynamically irradiate the surface of the personal equipment. It is to be understood that the aura generated by the UV array of the personal equipment may be continuous or several auras of UV radiations can be produced by the personal equipment. Additionally, the aura has no fixed boundaries, but a space having an average intensity of the UV radiations, also referred herein as the aura zone or UV zone.

It is to be understood that the present invention has been described using the UV-C radiation source in the personal equipment for killing the microorganisms, however, all types of microbiocidal radiation sources are within the scope of the present invention.

Referring to FIG. 1, which shows an exemplary embodiment of the personal equipment which is a headgear 100 configured to cover the head of a person, and more specifically a helmet. Helmets are used in a variety of activities to protect the head from injury, such as during driving, sports, constructions, and like activities. The headgear 100 can include a face opening along the periphery of which embeds a continuous UV array 110. The UV array 110 produces an aura 120 in spatial relationship with the face opening of the helmet. The aura is shown by a cloud and it can be seen that the UV radiations (shown by mesh) are in front of the headgear and the inner of the headgear is not exposed to the UV radiations. Therefore, the wearer of the helmet can safely wear the headgear without any risk of being exposed to the radiations. If any radiations may reach the face of the wearer, such radiation may be of an intensity not harmful to humans. Moreover, the intensity and the type of the UV radiation can be such as not to harm humans but to kill the targeted microorganisms, including viruses, an example of such UV radiation is the far UV-C radiation. The breathing of the wearer is shown by a cloud in front of the face opening of the headgear. It can be seen in FIG. 1 that aura 120 is within the mesh, which can reduce the harmful microbiological load in both the air being inhaled and exhaled in near real-time. To further narrow down the exposure of the wearer to the UV radiations, the array of LEDs is arranged such as to produce cross light beams which disperse and interfere, creating interfering light patterns, which maintain high UV radiations intensity at a greater distance away from the face of the wearer and in front of it. For example, by producing far UV-C radiations of adequate intensity and special dispersion and creating adequate interference of far UV-C radiations around the face of the user, any exposed body parts of the user, including face, hands, skin, eyes, etc. would be safe. The aura zone in front of the user's face reduces the harmful microbiological load in the air in the frontal immediate vicinity of the face. Practically, the wearer will be breathing the air from the UV aura. This can be of an advantage as the majority of the airborne infections are spread through fine liquid droplets or aerosols that become airborne when infected people cough, sneeze, or talk.

It has been demonstrated in the art that the far-UV-C light can efficiently kill aerosolized influenza virus in the air, in a setting similar to a public space. Far-UV-C light efficiently inactivated aerosolized H1N1 virus, a common strain of flu virus, in a test chamber exposed to very low doses of 222 nm far-UV-C light. Additionally, the limited exposure to the far-field UV-C light has been demonstrated to be safe for humans. The use of overhead low-level far-UV-C light is shown to be a safe and efficient method for limiting the transmission and spread of airborne-mediated microbiological diseases, like coronaviruses, SARS-CoV-2, influenza, and harmful bacteria such as Staphylococci, Streptococci, and tuberculosis. It has been demonstrated in the art that the UV light intensity sufficient to inactivate a coronavirus is 4.75 $J/cm^2$. An 8 W far-UV-C LED can provide about 8 J/s UV light or 8 J for one second of exposure. The disclosed headgear can have the arrangement of LEDs spaced 1 cm apart that could provide more than 4.74 $J/cm^2$ in the vicinity of the face of the user, which can protect the face of a wearer from being bombarded by airborne harmful microorganisms, including SARS-family viruses, without the need for wearing unreliable face masks, screen shields, or any other face-protecting gear.

Each LED can be housed in a housing that allows controlling the angle of the LED for creating the desired UV interference resulting in the UV aura. The UV LEDs can be powered by a power unit also housed in the headgear. For example, the power unit can include a battery, preferably a rechargeable battery, such as lithium-ion battery. Moreover, the disclosed headgear can also include a controller 130 for configuring the UV LEDs, fully controlling them, and turning them on and off. The headgear can also include a sensor (not shown) that can detect the presence of a subject or an object in the proximity of the wearer that may be approaching the wearer, or the wearer approaching the object/subject. The controller can receive a signal from the sensor indicating the presence of the object/subject within the predetermined distance, turn the UV LEDs on and turn off the same when the object/subject leaves the pre-programmed vicinity of the wearer.

Figure 2:
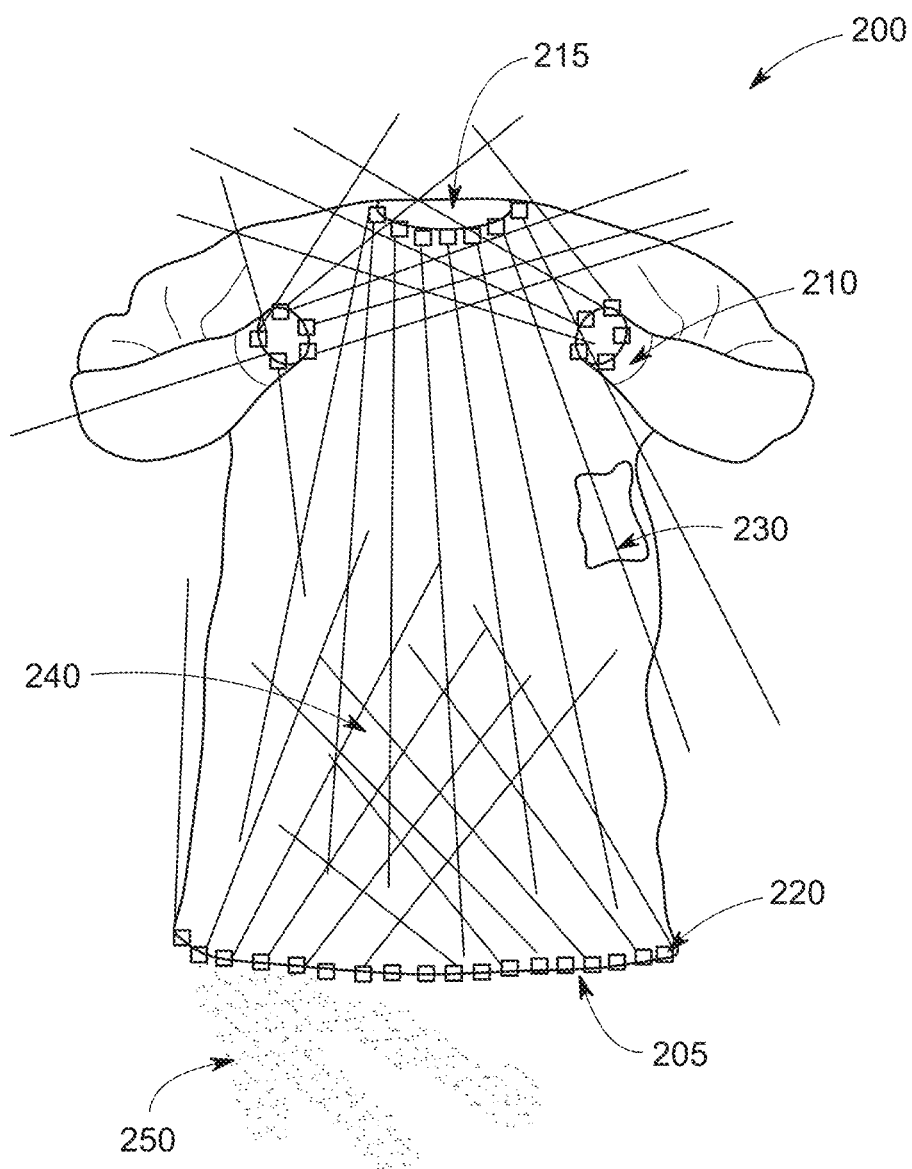
FIG. 2 shows another exemplary embodiment of the personal equipment which is a surgical gown embedded with an array of UV LEDs, according to the present invention.

FIG. 2 shows another exemplary embodiment of the personal equipment which is a surgical gown 200 having a bottom edge 205, cuffs 210, and a neck edge 215 all containing the LED array 220. A controller 230 can also be seen coupled to the surgical gown 200. The controller and the UV LEDs can be powered by a power unit (not shown) also housed in the surgical gown 200. The interference of the UV radiations is shown as a mesh 240 in spatial relationship with the surgical gown. The multiple and various dispersing and interfering patterns of the individual light beams produced by the different LEDs increase the chances to neutralize more and more microbiological contaminating particles dynamically attacking the user as the user moves while wearing the gown. The interference of the light beams produces an aura 250 that can be continuously forming a virtual barrier to microbiological contaminants, including viruses.

Figure 3:
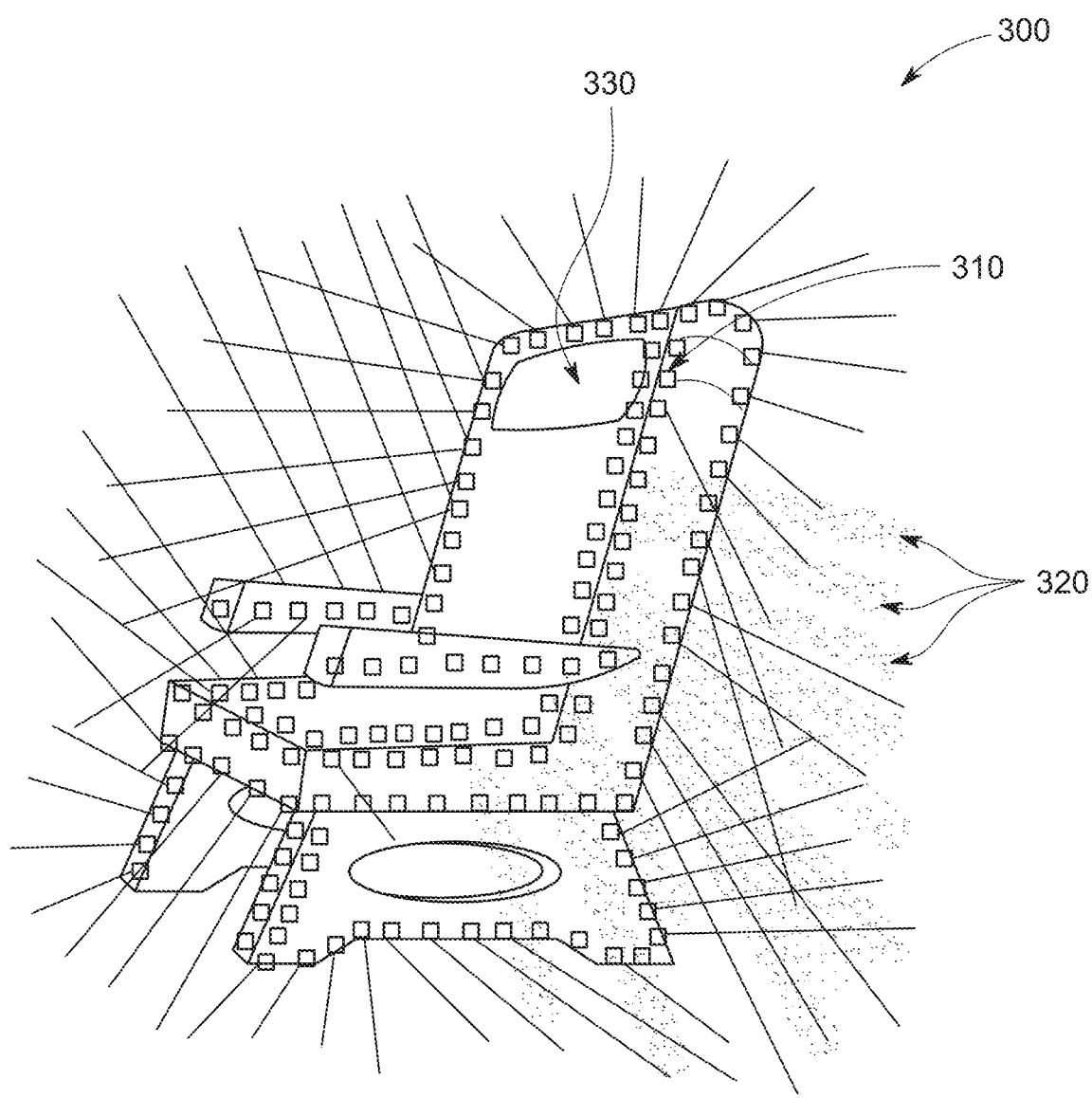
FIG. 3 shows another exemplary embodiment of the personal equipment as a seat embedded with an array of UV LEDs, according to the present invention.

Referring to FIG. 3, which shows a chair 300, which can be any utility chair, such as public transport seat, a seat at a public place, a seat in a restaurant, and like. The LEDs array 310 can be seen along the edges of the chair and configured to produce the interfering aura pattern 320 near seat 300. A control panel 330 can also be seen on the front side of chair 300. In the case of airplane seats, there can be no need for maintaining the social distance between the users in adjacent seats, as long as the protective auras of adjacent seats are turned on creating a virtual barrier between the adjacent persons. The same protection can be provided to toilet seats and sinks, as well as in the entire compartments of planes, cars, trains, and other means of public transportation. The movement of passengers around would only enhance their protection, rather than disturbing it, particularly if they are asked to wear personal UV LED protective garments as well.

Figure 4:
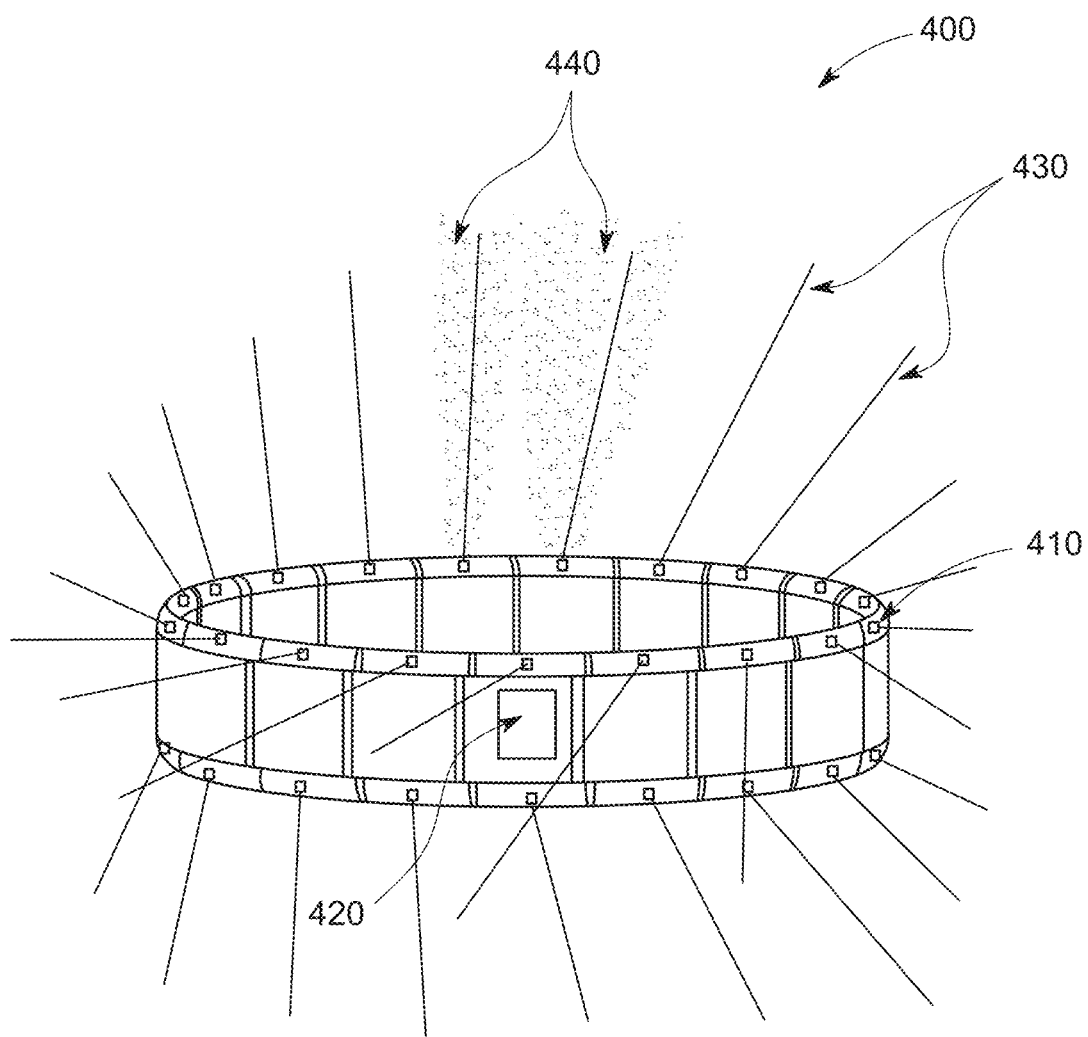
FIG. 4 shows another exemplary embodiment of the personal equipment as a bracelet embedded with an array of UV LEDs, according to the present invention.

FIG. 4 shows a bracelet 400 that can be worn in an arm of a user. The bracelet can include elements bound together in a stretchable fashion so that the bracelet can be worn in different size wrist and/or ankle diameters. The bracelet 400 includes a matrix of UV LEDs 410 arranged appropriately so that they emit UV light under the control of the power supplying and controlling module 420, the light being emitted in the general directions shown by lines 430, with the emitted light beams having dispersion and interfering patterns shown by a cloud 440. The bracelet when worn on the wrist can protect the hand from contaminated objects getting in touch with the hand. Similarly, accessories can be worn on the ankle or toe of a foot for protection.

Figure 5:
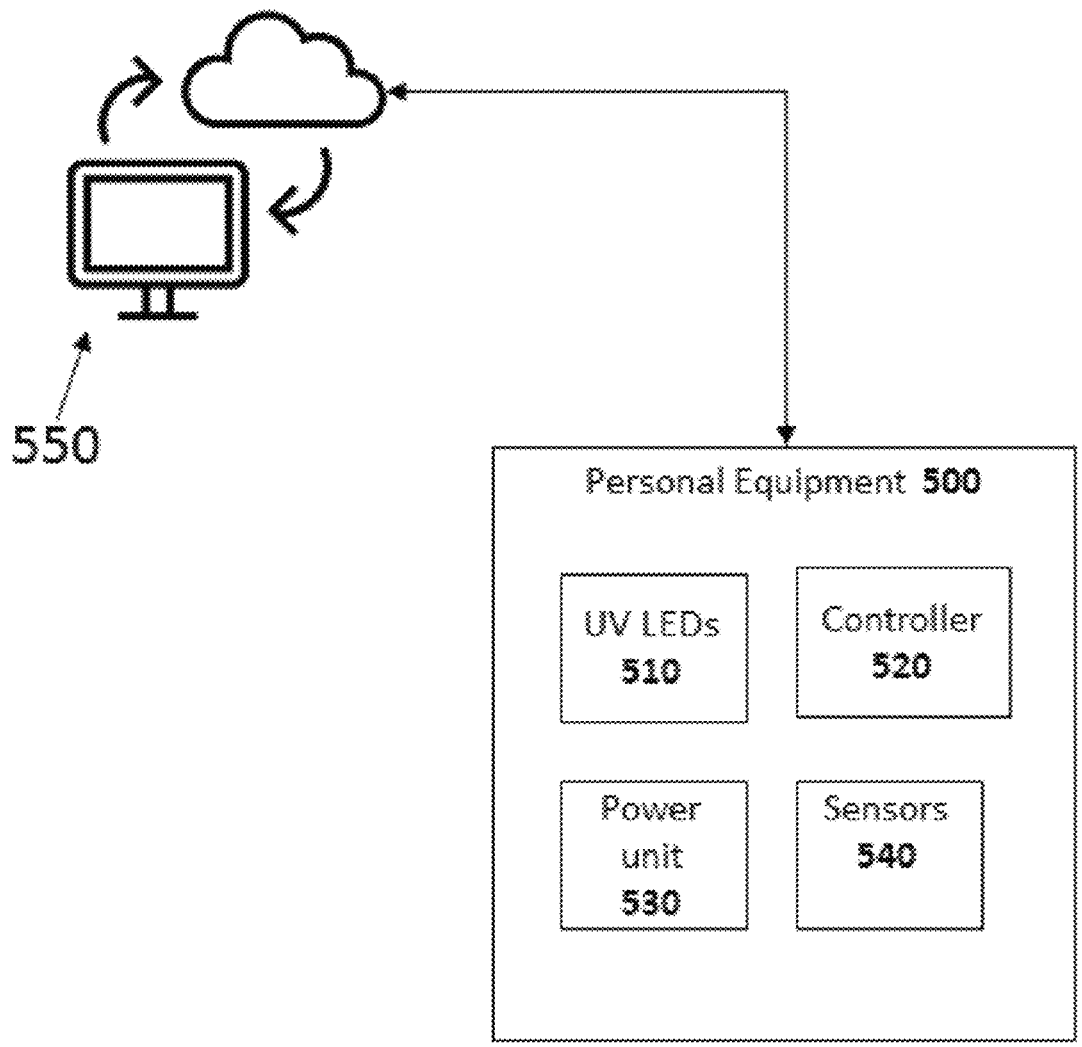
FIG. 5 is a block diagram of the disclosed personal equipment having the UV light source, power unit, sensor unit, and a control unit, according to an exemplary embodiment of the present invention.

Referring to FIG. 5 which is a block diagram showing the disclosed personal equipment 500 that may include a plurality of UV LEDs 510, a controller 520, and a power unit 530 for powering the UV LEDs and the controller. Personal equipment can be embodied as any utility article related to a user, such as clothing. The plurality of UV LEDs can be arranged in arrays to provide UV radiations that result in an interference creating a UV aura in spatial relationship with the personal equipment. The UV aura can have sufficient energy to kill the harmful microorganisms, including viruses dispersed in the air coming in contact with the UV aura.

The personal equipment can also include the sensors 540 that can determine whether an object is near the user and if so, the power supply and control module can turn on the protective UV light aura around the user until objects are no longer present in the predetermined vicinity. This could save significant electrical power. The sensors can widely vary and can include position sensors, UV light intensity sensors, sensors of temperature, air quality, moisture, acceleration, and other physical, chemical, biochemical, physiological, biological, electrical parameters or combinations thereof. A miniature position sensor can be supplied, for example, by TE Connectivity, Berwyn, Pa. 19312. The recognition feature can be made more sophisticated by utilizing pattern and image recognition and artificial intelligence to discriminate between unsafe or unknown objects and/or subjects and safe objects and subjects, such as family members, houses, or objects known to be safe for the user. The personal equipment can also be connected to an external computing device 550 for configuring the equipment. The personal equipment can be connected through a wired or wireless connection.

While the foregoing written description of the invention enables one of ordinary skill to make and use what is considered presently to be the best mode thereof, those of ordinary skill will understand and appreciate the existence of variations, combinations, and equivalents of the specific embodiments, methods, and examples herein. The invention should therefore not be limited by the above-described embodiments, methods, and examples, but by all embodiments and methods within the scope and spirit of the invention as claimed.

What is claimed is:

1. A wearable utility article comprising:

an arrayed plurality of individually-housed far UV-C LEDs arranged in the wearable utility article and configured in cooperative individually controllable relationship with a controller to produce a respective plurality of individually angularly-controllable crossing light beams of far UV-C radiation which disperse and interfere with one another in variably interfering light patterns of far UV-C radiation intensity harmful to microorganisms and pathogens to decrease a harmful microbiological load at a zone of variably adjustable range from, and in front of, a face of a person when wearing the utility article, while maintaining a lesser far UV-C radiation intensity safe to humans where the face of the person resides when wearing the utility article, wherein each individual LED of the arrayed plurality of individually-housed far UV-C LEDs is individually housed in a respective housing configured for individual control, by the controller, over a respective angle of said individual LED of the arrayed plurality of individually-housed far UV-C LEDs relative to other individual LEDs of the arrayed plurality of individually-housed far UV-C LEDs to thereby change from one of said variably interfering lights patterns between the individually angularly-controllable light beams of the arrayed plurality of individually housed far UV-C LEDs to a different one of said variably interfering lights patterns.

2. A method for reducing a harmful microbiological load in a vicinity of a utility article, the method comprising the steps of:

donning the wearable utility article of claim 1; and turning on a power supply to the arrayed plurality of individually-housed far UV-C LEDs, thereby casting one of said variably interfering light patterns at said zone of variably adjustable range; and changing, by the controller, of said respective angle of at least one LED of said arrayed plurality of individually-housed far UV-C LEDs relative to at least one other LED of said arrayed plurality of individually-housed far UV-C LEDs, thereby changing said interference patterns between the respective plurality of individually angularly-controllable light beams.

* * * * *